United States Patent [19]
Yamashita et al.

[11] 3,976,049
[45] Aug. 24, 1976

[54] STRUCTURE OF WARMER

[75] Inventors: Iwao Yamashita; Miyuki Shimizu, both of Oitashi, Japan

[73] Assignee: Asahi Kasei Kogyo Kabushiki Kaisha, Tokyo, Japan

[22] Filed: June 28, 1974

[21] Appl. No.: 484,236

[30] Foreign Application Priority Data

| July 4, 1973 | Japan | 48-74737 |
| Sept. 8, 1973 | Japan | 48-101485 |
| Jan. 10, 1974 | Japan | 49-5613 |
| Feb. 27, 1974 | Japan | 49-22383 |
| Jan. 5, 1974 | Japan | 49-5652[U] |

[52] U.S. Cl. ............... 126/263; 126/204; 44/3 A; 128/254; 128/403
[51] Int. Cl.² ............................................ F24J 1/00
[58] Field of Search ............ 44/3 A; 126/263, 204, 126/400; 128/254, 399, 403; 229/3.5 R

[56] References Cited
UNITED STATES PATENTS

| 1,434,576 | 11/1922 | Werthmimer | 126/263 |
| 1,819,807 | 8/1931 | Baysinger | 126/263 X |
| 1,901,313 | 3/1933 | Mann | 44/3 A |
| 1,910,874 | 5/1933 | Ziegler | 44/3 A |
| 2,157,169 | 5/1939 | Foster | 126/263 |
| 2,573,791 | 11/1951 | Howells | 128/254 X |
| 2,680,063 | 6/1954 | Shapiro | 126/263 X |
| 3,301,250 | 1/1967 | Glasser | 126/263 |

*Primary Examiner*—John J. Camby
*Assistant Examiner*—Henry C. Yuen
*Attorney, Agent, or Firm*—Armstrong, Nikaido & Wegner

[57] ABSTRACT

A unified structure of a warmer is obtained by accommodating an exothermic composition consisting of iron powder, a chloride or sulfate of a metal having a tendency of ionization greater than iron, active carbon and water in a bag composed of a cloth or cloths and a film or films having aeration holes and encapsulating the resulting warmer in an air-tight envelope. Heat of oxidation of iron powder is utilized for the purpose for creating and keeping warmth.

15 Claims, 11 Drawing Figures

STRUCTURE OF WARMER

DESCRIPTION OF THE INVENTION

This invention relates to warmers' structures.

There have been heretofore known warmers which utilize the heat generated by supplying suitable amounts of water and air to iron powder followed by oxidation of the same.

For example, the specification of U.S. Pat. No. 3,301,250 discloses a porous fabric bag capable of permeating an oxygen-containing atmospheric gas, filled with a uniform mixture of inorganic porous materials, iron powder, inorganic salts and water containing a wetting agent and capable of generating heat when exposed to the atmospheric air. This conventional flameless heater is formed by filling a mixture consisting of expanded inorganic porous materials such as vermiculite, iron powder, inorganic salts such as ammonium chloride and water containing a wetting agent into a porous fabric bag having air-permeability and sealing the bag. This warmer has a sealed structure of plastics bag prepared from plastics films consisting of two layers of a cellulosic resin and polyethylene resin.

Since the conventional warmer as above-mentioned utilizes only one layer of cloth for its outer part i.e. in the bag part, it is not possible to alter duration time of heat-generation or to control heat-generating temperature when the body is in service in order to attain its object.

In the above-mentioned prior art, there are set forth methods for changing heat-generating temperature and duration time by changing the kinds of cloths, widening or narrowing interstices of cloths, but it is impossible to change the above-mentioned temperature or time while fixing the kind of cloth.

Further, since the above-mentioned warmer has such constitutional conditions as above-mentioned, it is impossible to prevent escape of steam formed by the heat-generation of the composition enveloped therein, and due to this escape of water, the iron powder does not contribute to the heat-generating reaction for a long time. Moreover, there is a danger of the composition encapsulated in the inside, being leaked through the interstices of fabrics and it has a drawback in that they cannot be used for the applications in which adhesion of leaked composition should be avoided. Further since vermiculite which is a physically inactive substance is used in the composition contained in the above-mentioned warmer, it has a poor compatibility with iron and inorganic salt and on this account a wetting agent must be used additionally. Further since vermiculite has a small inside surface area, its moisture-retention capacity is extremely weak. In the above-mentioned composition, there is used ammonium chloride to promote oxidation reaction of iron. Since the ammonium chloride has a lower decomposition temperature, the composition evolves ammonia gas at the time of its heat-generation and gives offensive odour. Thus the warmer containing ammonium chloride in the composition cannot be applied to living things and its utility is inevitably limited.

In the heat-generating compositions which contain the above-mentioned iron powder as a principal heat-generating agent, some kinds of iron powder to be added therein show only a slow heat-generating property or often no heat-generating property.

A principal object of the present invention is to provide a structure of warmer which can be applied for warming human body, particularly for warming affected part for curative purpose.

Another object of the present invention is to provide a structure of warmer which can be applied for wide varieties of uses as a heat source and a source for keeping warmth in personal belongings and a household first-aid outfit.

A further object of the present invention is to provide a heat-generating warm stupe structure effective to medical treatment by providing a stupe layer to the above-mentioned structure.

A further more object of the present invention is to provide a structure of warmer which is light in weight and simple in handling and yet having no drawbacks of conventional warmers such as those set forth above.

A first characteristic feature of the present invention is the use of a unified material of cloth and air-permeable film as a construction material of bag. Since the film which is a part of the construction material of this bag is provided with fixed aeration holes, it is possible to control the amount of permeation of air through the construction material and hence it is possible to maintain the heat-generating temperature and duration time of heat-generating composition.

A second characteristic feature of the present invention is the use of a film in a part of construction material of the bag as above-mentioned by which the escape of the steam produced by the heat-generation of the heat-generating composition, to the outside of the bag can be prevented and the heat-generating reaction can be continued for a long period of time. Further the use of a film can prevent the leakage of the fine powder of the heat-generating composition encapsulated therein and thus this is an essential requirement for attaining the object of the present invention. The reason is as follows: As for the bag consisting of a unified material of film and cloth, to be used in the present invention, a fixed one can be used in the range capable of preventing the leakage of the heat-generating composition, and hence there is no need of altering the kind of cloth for controlling the amount of air permeation.

A further important characteristic feature of the present invention lies in that the heat-generating composition contains, as one component, active carbon. Since active carbon is extremely porous and activated, it absorbs water in the composition very well and makes the contact with iron powder better. Accordingly, there is no need of further addition of a wetting agent. Since active carbon has not only a strong water-absorbing property but also a superior moisture retention capacity, it again adsorbs water vapour evaporated by the heat generation of the heat-generating composition, and thus prevents the escape of water vapor from the composition. Since the presence of active carbon enables to supply water until all of the iron powder in the heat-generating composition is completely oxidized, it is an essential component in the warmer of the present invention.

A further characteristic feature of the present invention is the use of a metal chloride or sulfate, particularly potassium chloride, sodium chloride, calcium chloride or magnesium chloride which are not harmful to human and other living things, as an oxidation promoter of iron powder.

A further feature of the present invention is the addition of an element or a compound of chromium, manganese, copper or a mixture thereof to the heat-generating mixture as an oxidation catalyst of iron powder included therein. The addition of a small amount of these materials enables to oxidize all of the iron powder.

A still further feature of the present invention lies in that the part of bag of the warmer has a unified structure of body of cloth layer and film layer and heat-sealing is applicable in bag forming, which enables to shape a large number of bags within a short time.

In connection with the above-mentioned features, there is another characteristic feature that if a non-woven fabric is used for a cloth of the cloth layer, a light and strong bag for keeping warmth can be provided and a larger number of such bags can be produced within a shorter time.

It is to be noted that the application fields of the structure of the warmers of the present invention are not limited to those of the above-mentioned various characteristic features and the warmers of the present invention have superior characteristic features applicable in all kinds of object and utility.

The descriptions of the objects and characteristic features of the warmers have been made thus far, but other objects, features and advantages thereof will be understood by referring to the detailed description of the specification and claims and accompanying drawings. However, preferred embodiments shown in the specification and appended drawings are only illustrative and not intended to be limitative of the scope of the invention claimed.

Figure 1:
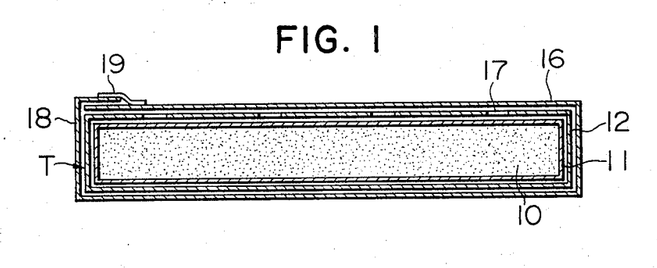
FIG. 1 is a cross-sectional view of one embodiment of the warmers of the present invention.

An inner bag 11 is a holder for accommodating a heat-generating composition 10. A cloth which does not allow the accommodated heat-generating composition 10 to leak to the outside and has an amount of air permeation in the range of 9,000–10 cc/cm$^2$. min. as measured according to Frazier type method is used. As cloths, cotton cloths, synthetic fiber cloths, mixed spun cloths of these fibers, non-woven cloths, etc. are used.

A middle bag 12 has objects of preventing the leakage of heat-generating composition 10, controlling the vaporization of moisture included in the heat-generating composition 10 and preventing the intrusion of air except through aeration holes 17. As the materials, sheets or films of high molecular weight compounds e.g. polyethylene, polypropylene, nylon, polyester, polyvinyl chloride, polyvinylidene chloride, polystyrene, natural rubber, synthetic rubbers, reclaimed rubbers, etc. whose air permeabilities are 0.001 cc/cm$^2$. min. or less as measured by the air-permeation test according to Frazier type method are used. Aeration holes 17 are provided to supply outside air to the composition 10 in the inner bag 11. They have usually circular shape but those having shapes other than circular are also useful so long as they serve the purpose. As for the number and size of these aeration holes 17, when the ratio of the total area of the holes are 0.1–5percent per total surface area of this inner bag and the amount of air permeation is in the range of 0.5–400 cc/cm$^2$. min., preferably in the range of 1–150 cc/cm$^2$. min., as measured by the air permeation test according to Frazier type method, excellent heat-generating effectiveness can be attained.

Air-tight envelope 16 which is an outer bag is used to isolate the inside composition 10 from the outside air at the time of storage of the warmer or at the time of interruption of heat-generation and air-impermeable sheets or films of high molecular weight compounds are used as such envelope. As for its material, the same materials with those used for the middle bag 12 are generally used. It is possible to use a laminate for the air-tight envelope 16. So long as air-tightness can be held, other vessels can also be used. The sealing part 19 of the air-tight envelope 16 can be sealed in a suitable sealing manner. As such, those which rely on adhesive tapes, heat-sealing, fastener, etc. are illustrated but other sealing means can also be utilized.

The heat-generating composition 10 is a principal element for the function of the structure of warmer of the present invention. Iron powder is a principal heat-generating agent to which a reaction-promoter, a wetting agent, water and if necessary, other additives are added.

As for iron powder, there are illustrated cast iron powder, reduced iron powder, electrolytic iron powder, scrap iron powder, etc. There is no particular limitation to their shape, purity, kind, etc. so long as heat-generation with water and air can be confirmed.

Reaction promoter is a medium for activating the surface of iron powder to ease the oxidation reaction with air. For example, there are illustrated sulfates such as ferric sulfate, potassium sulfate, sodium sulfate, magnesium sulfate, etc. and chlorides such as potassium chloride, sodium chloride, calcium chloride, magnesium chloride, etc. Among them, sodium chloride shows small solubility difference vs. temperature difference and hence no crystal is precipitated at low temperatures, and also heat-generation occurs very well. Thus, deviation of heat-generation due to temperature difference of atmospheric air does not occur.

Deliquescent chlorides such as calcium chloride, magnesium chloride, etc. have a large water-retention property and hence these compounds, even when added in a small amount, show an effectiveness of aiding the water-retention property of active carbon, that is, that of inhibiting the escape of water vapour. Since these reaction promoters are water-soluble, they show better effect when they are added in the dissolved state in water than in the solid state because they contact uniformly with iron powder.

As for the amount of these reaction promoters to be added, 0.5–30 parts by weight per 100 parts by weight of iron powder gives preferable result. The amount of addition greater than 30 parts by weight is not only uneconomical but rather harmful because these promoters adhere to the surfaces of iron powder and wet-keeping material and prevent their reaction or function. The amount of addition less than 0.5 parts by weight does not produce desired heat generation because their function as activating catalyst becomes weaker.

Active carbon i.e. a wet-keeping material which is one component of the composition 10 absorbs the above-mentioned aqueous solution of reaction promoter and performs a function of gradually supplying the promoter and water to the coexistent iron powder.

This wet-keeping material has not only the above-mentioned wet-keeping function for the aqueous solution but also a warmth-keeping function. As for such wet-keeping material, porous silicates, wood powder, cotton cloth having a large amount of fluffs, short fibers of cotton, paper scrap, etc. or active carbon and other porous materials having a large capillary function and hydrophilic property can be used. Among these wet-keeping materials, active carbon has particularly superior water-retention capability. Since active carbon is extremely porous in the inner structure and is activated, it absorbs the aqueous solution of the composition 10. Moreover, active carbon not only absorbs water well as mentioned above, but also adsorbs water vapor evaporated by the heat generation of the heat-generating composition 10 due to its superior adsorptivity and prevents the escape of the water vapor. Thus active carbon included in the heat-generating composition can supply water until all of the iron powder in the composition 10 are completely oxidized, on account of its superior water-retention capacity as above-mentioned. Further since this active carbon has simultaneously a capability of adsorbing a nasty odour caused by the oxidation of iron powder which is referred to commonly as iron rust odour, the object of the warmer of this invention i.e. applications to the warmth-keeping and medical care of human bodies and a wider variety of other uses can be realized.

As for active carbon, those prepared e.g. from coconut shell charcoal, coal, bone coal, etc. are useful, but those prepared from other raw materials are also useful. In short there is no limitation to the kind so long as they have superior water-retention capacity.

With regard to the particle size of the active carbon used for the warmer of the present invention, those of $104\mu$ or smaller are effective. If the size exceeds $104\mu$, the water-retention capacity of active carbon is gradually lowered.

It is effective to incorporate active carbon in the heat-generating composition 10 in the range of 2.5–400 parts by weight per 100 parts by weight of iron powder. If the amount of incorporation is less than 2.5 parts by weight, water-retention effect and water-absorbing effect are reduced. Incorporation of more than 400 parts by weight reduces heat-generating effect. It is preferable to cause active carbon to absorb, in advance, water or an aqueous solution of a reaction promoter. As for the amount of water or an aqueous solution to be absorbed by the active carbon, a range of 10–250 parts by weight per 100 parts by weight of active carbon gives a preferable result.

The above-mentioned components of the composition are blended while being isolated from air, filled in the above-mentioned inner bag 11 and sealed to form a structure of warmer T. This structure is further contained in an air-tight envelope 16 and sealed to complete a unified structure of a warmer.

In the structure of the warmer of the present invention, when the sealing part 19 of the air-tight envelope 16 provided with a sealing means is released, an opening part 18 is opened and the warmer T is taken out, outside air flows in the heat-generating compostion 10 through aeration holes 17 for the composition and inner bag 11 inside the warmer T, and heat-generation is immediately initiated. When interruption of heat-generation is desired, all that is required is to return the contents into the air-tight envelope.

Figure 2:
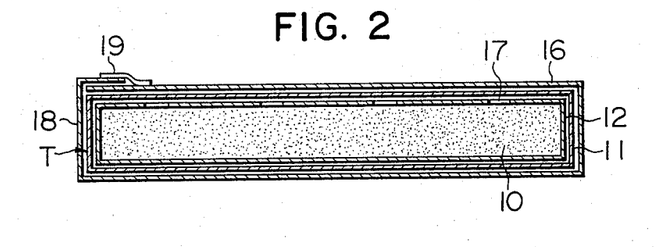
FIG. 2 is a cross-sectional view of one embodiment different from that of FIG. 1, of the warmers of the present invention.
Figure 3:
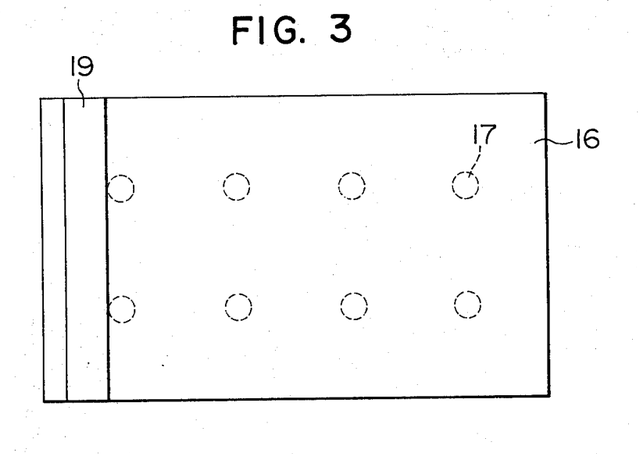
FIG. 3 is a plan view of the warmers of the present invention according to the embodiments of FIGS. 1 and 2.

FIG. 2 shows a structure in which the positions of the inner bag 11 and the intermediate bag 12 are interchanged. Its constituting materials, heat-generating composition, heat-generating mechanism, function, operational conditions, etc. are entirely same with those of the structure shown in FIG. 1. FIG. 3 is a plan view of the structures of FIGS. 1 and 2 in which numeral 16 is an air-tight envelope, 17 is aeration holes and 19 is a sealing part.

Figure 4:
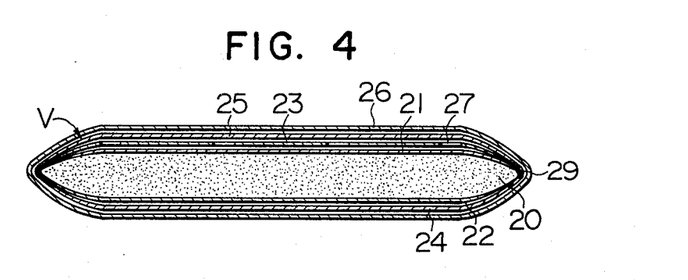
FIG. 4 is a cross-sectional view of a further embodiment of the warmers of the present invention.

FIG. 4 shows by a cross-sectional view, one example of the embodiments of the present invention in which a heat-generating composition is filled in a modified bag consisting of three upper covering layers and two lower covering layers, closed, contained in an air-tight envelope and sealed to form a unified body.

In the structure shown in FIG. 4, the warmer V has a modified bag whose upper covering layers consist of a non-woven fabric 21, a film 23 having aeration holes 27 and a non-woven fabric 25 in the order counting from the inside and whose lower covering layers consist of a film 22 and a non-woven fabric 25 in the order counting from the inside. The three upper covering layers and the two lower covering layers of the warmer V are sealingly adhered along their peripheral parts 29. For sealing this warmer V, three upper covering layers and two lower covering layers of this body V are sealingly adhered at first along the peripheral parts 29 of three sides thereof, then a heat-generating composition 20 is contained and the remaining side is sealed.

The warmer V thus constructed is inserted in an air-tight envelope 26, and sealed to complete a unified structure of a warmer.

The structure of a warmer shown in this example is a type which is obtained by providing further a cloth layer (a non-woven fabric is used in this embodiment) under the upper covering layer of the inner bag 12 of the structure shown in FIG. 2. By providing this non-woven cloth layer, it is intended to prevent the heat-generating composition from leaking through aeration holes 27 of film 23. For the non-woven fabrics used as the construction material of the structure shown in FIG. 4, those prepared from nylon, polyester, cuproammonium cellulose (Bemberg) and other high molecular weight compounds are suitable. In spite of fine interstices, these non-woven fabrics show excellent air-permeability and characteristic properties in the light weight and strong tensile strength.

For other construction materials and heat-generating composition used in the structure of this embodiment, the same materials and the same composition as those used in the embodiment shown in FIG. 1 are suitable.

Figure 5:
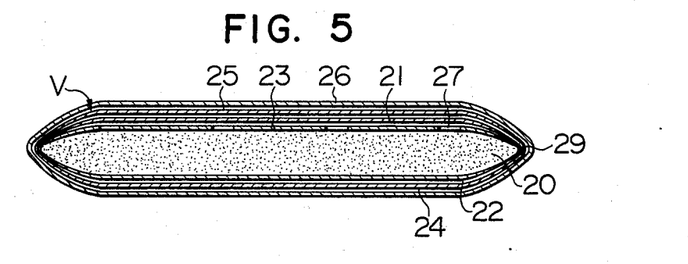
FIG. 5 is a cross-sectional view of a still further embodiment of the warmers of the present invention.

FIG. 5 is a cross-sectional view of the structure obtained by interchanging the positions of non-woven fabric 21 and film 23 in the structure shown in FIG. 4. The same construction materials and the same heat-generating composition are used as in the embodiment shown in FIG. 4.

Further, the heat-generating mechanism, operational conditions, etc. of the structures shown in FIGS. 4 and 5 are entirely the same with those of the embodiment shown in FIG. 1.

Figure 7:
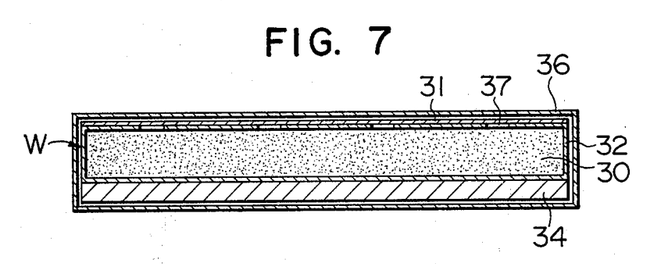
FIG. 7 is a cross-sectional view of the warmers of the present invention in which a stupe layer is provided to form a unified structure with the warmers.

FIG. 7 is a cross-sectional view of the structure of a still further embodiment of the present invention. A stupe layer is attached to the warmer T which is a principal constitutional thing of the present invention to form a unified heat-generating stupe body which is further encapsulated in an air-tight envelope and then sealed to form one body.

Film 32 is the same with the inner bag 11 of the structure shown in FIG. 1 and provided with aeration holes 37. A cloth layer 31 is adhered onto the upper surface of the film 32 and a stupe layer 34 is formed under the lower surface of the film 32. A heat-generating composition 30 is accommodated in the resultant unified bag and sealing is made to form a heat-generating stupe body W.

The constructional materials, the heat-generating mechanism, operational conditions, etc. in the embodiment shown in FIG. 7 are all same with those of the structure shown in FIG. 1.

The stupe layer 34 is a layer for holding water or stupe medicine such as a medical solution for stupe, a paste for stupe, etc. and applying a warm stupe to skins. Materials of a high molecular weight substance which show capillary phenomenon, such as paper, woven cloths, non-woven fabrics, continuous sponge, etc., are used in multiple laminated form. It is preferable to use materials such as gauze, cotton or the like which are agreeable in the touch on the side to be contacted with skin.

This stupe layer 34 is adhered to the underside surface of the stupe body W i.e. the underside surface of the film 32. In such a case it may be possible to adhere a stupe layer impregnated with a medical solution for stupe but better adhesion can be attained when the stupe layer is adhered before it is impregnated with a stupe solution.

This stupe layer 34 can take the state impregnated with water or a medical solution or the state which is not impregnated therewith depending upon the object of the application. In any case, this stupe layer 34 is combined with a stupe body W containing accommodated heat-generating composition 30 to form a unified body inserted in an air-tight envelope 36 sealingly to complete a unitary heat-generating warm-stupe body.

For stupe solutions to be impregnated in the above-mentioned stupe layer 34, conventional solutions such as simple water, aqueous boric acid solution, aqueous sugar of lead solution, saline water, aqueous alcoholic solution, linseed oil-lime water, cod-liver oil, olive oil, aqueous rivanol solution, menthol, methyl salicylate, mint oil, etc. and novel stupe medicines are all useful.

Description will be given with regard to a still more embodiment of the present invention in which a catalyst is added to the components of the above-mentioned heat-generating composition.

Iron powder usually undergoes oxidation reaction and generates heat when it is used as a heat-generating component of the above-mentioned heat-generating composition, but a certain kind of iron powder shows only a only a slow-oxidative property and also there is a kind which does not undergo oxidation. On this count, difficulty has been brought about in the selection of iron powder.

We have discovered that the addition of elements, compounds or their mixtures of chromium, manganese or copper in a very small amount to the iron powder whose oxidative property is slow or nil makes the latter extremely oxidizable. Thus any kinds of iron powder undergo oxidation reaction very well by adding a small amount of the above-mentioned catalyst to the iron powder according to this discovery and enables to perform the object. Accordingly, there is no more difficulty brought about in the selection of iron powder.

If the catalyst to be added to the iron powder is used in an amount of 100 ppm or more in case of chromium, 500 ppm or more in case of manganese, and 80 ppm or more in case of copper, each as calculated as an elemental metal, and based upon 100 parts by weight of iron powder, the above-mentioned object can be attained. Even when these catalysts are added in the form that these components are included in iron powder as its inherent components, they do not give any influence upon the object of the invention.

As a still further embodiment of this invention, the warmers of the present invention can take the following construction in its bag part. For example, for the inner bag 11 and the intermediate bag 12 shown in FIGS. 1 and 2 i.e. the cloth layer and the film layer, and also for the upper covering layers, i.e. non-woven cloth layer 25, film layer 23, non-woven cloth layer 21 and the lower covering layers i.e. the film layer 22 and non-woven cloth layer 24, shown in FIGS. 4 and 5, those which have been processed into laminates can be used.

In short as construction materials of bag in case of the embodiments of FIGS. 1 and 2, two layers of cloth and film can be made into a laminated sheet and in case of the embodiments of FIGS. 4 and 5, the three upper covering layers and the two lower covering layers are made into laminated sheets, respectively.

When laminated sheets thus formed are used as construction materials of bag, following advantages can be attained, compared with the construction of bags used in the above-mentioned embodiments shown in FIGS. 1–6.

1. Since there is no vacant space between the cloth layer and the film layer, bags show less bulkiness.
2. The strength of bags becomes greater because of laminated state.
3. Since there is no heat-generating composition between the cloth layer and the film layer, no deviation of heat-generating temperature occurs.

It is also possible to provide a following means i.e. although there is provided aeration holes in the upper covering film layer of a bag shown in the drawing, it is also possible to provide aeration holes also in the lower covering film layer.

Thus far detailed explanation has been made with regard to preferable embodiments of the present invention but it is apparent that different embodiments can be constituted within the scope of the claimed invention without departing the spirit and idea of the present invention. Accordingly the present invention is not limited by specific embodiments so long as it is within the scope of the appended claims.

EXAMPLE 1

A structure of warmer having a construction shown in FIG. 1 and an effective amount of air permeation of 3.6 cc/cm$_2$. min. was prepared using a heat-generating composition, a cloth, a film and an air-tight envelope shown in Table 1. The resulting structure of warmer was put on a basket rack made of Saran (trademark of polyvinylidene chloride manufactured by Asahi Kasei Kogyo Kabushiki Kaisha, Japan). A CA (chromel-alumel) thermocouple was fixed onto the inner bag of the structure of warmer with an adhesive tape, to record temperature change on Multipen Recorder WA621-1 type (trademark, manufactured by Watanabe Sokki Co., Japan). A temperature was measured before taking off the air-tight envelope, and then change of temperature (temperature rise) was traced after said taking off of the air-tight envelope. As a result, it was confirmed that the warmth-keeping by generated heat lasted for a long time and also than an optimum amount of water to be added was present, as shown in Table 2.

Table 1

| | Material used | | Weight | |
|---|---|---|---|---|
| | | Experiment No. 1 | 2 | 3 |
| | Material | | | |
| Heat-generating composition | Cast iron powder | 30 g | 30 g | 30 g |
| | Ferric sulfate | 5 g | 5 g | 5 g |
| | Active carbon | 30 g | 30 g | 30 g |
| | Water | 2 g | 30 g | 50 g |
| Bag made of cloth | Velveteen; 1 mm thick; dimension, 80 mm × 130 mm Amount of air permeation: 420 cc/cm². min. | | | |
| Film | Polyethylene; 25 μ thick; dimension, 80 mm × 130 mm Amount of air permeation: 0.0004 cc/cm². min. 6 holes of 0.3 cm² were opened. | | | |
| Air-tight envelope | Polypropylene; 50 μ thick; dimention, 85 mm × 130 mm Amount of air permeation: 0.00003 cc/cm². min. | | | |

Notes:
1. Active carbon was impregnated with water.
2. For sealing the opening of the air-tight envelope for taking out the inner bag therefrom, a cellophane tape (manufactured by Sekisui Kagaku Co., Japan) was used.
3. The measurement of amount of air permeation according to Frazier type method was carried out using a textile air-permeability tester for Frazier type method, manufactured by Shimazu Seisakusho, Co. Ltd. Japan.

Table 2

Figure 8:
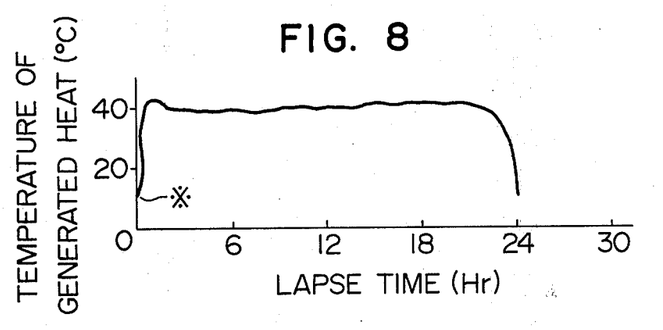
FIG. 8 is a graph showing the heat-generating status of the warmers of the present invention.

| Experiment No. | Result of measurement |
|---|---|
| | Temperature of warmer at the time of encapsulating in an air-tight envelope 13°C |
| 1 | Heat was generated up to a temperature of 43°C, but the period of time during which a temperature of 37°C or higher was maintained, lasted for about 1–2 hours. |
| 2 | Temperatures of 38°C–45°C were kept for about 23 hours, as shown in FIG. 8. |
| | Temperature rose up to 26°C, but, |

Table 2-continued

| Experiment No. | Result of measurement |
|---|---|
| 3 | after lapse of about 10 minutes, temperature showed a descending tendency. Even after the lapse of time thereafter, no heat-generating phenomenon was observed. |

Note: Environment temperature was 13°C.

EXAMPLE 2

Figure 9:
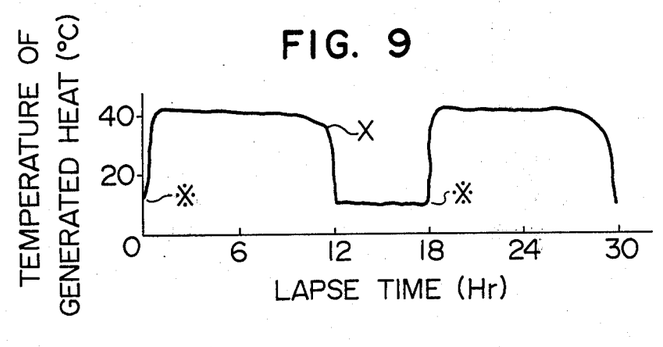
FIG. 9 is a graph showing the heat-generating status in case where heat-generation is interrupted in the midway and resumed again.

Experiment was carried out under the same conditions as in Example 1 except that the heat-generating composition of Experiment No. 2 in Example 1 was employed. On the way of testing, the inner bag containing the heat-generating composition was put in the air-tight envelope, which was then sealed to interrupt heat-generation. Thereafter it was taken out of the air-tight envelope, and heat-generation was resumed. Thus an experimental result shown in FIG. 9 was obtained. It was confirmed that even when heat-generation was interrupted halfway, subsequent heat-generation was resumable, and the subsequent state of heat-generation after the interruption and the resumption was identical to the initial state.

EXAMPLE 3

A structure of warmer was prepared with a construction shown in FIG. 2, using as a heatgenerating composition, the material of Experiment No. 2 in Example 1; as an inner bag, a material obtained by adhering a film having aeration holes bored as shown in Table 3 (material, polyester; 24μ thick; dimension, 80 mm × 130 mm; amount of air permeation, 2 × 10$^{-6}$ cc/cm². min.) onto one surface of a cloth bag (material, flannel; 0.9 mm thick; dimension, 80 mm × 130 mm; amount of air permeation, 540 cc/cm². min.), with a neoprene adhesive and an air-tight envelope (material, polyethylene; 40μ thick; dimension, 100 mm × 140 mm; amount of air permeation, 2 × 10$^{-4}$ cc/cm² . min.). The opening part of the air-tight envelope was sealed with Unipack (trade mark of a binding material manufactured by Seisannipponsha Co., Japan) to give a warmer.

Each warmer thus prepared was tested in the same manner as in Example 1. The results are shown in Table 4. It was confirmed through these results that even when a cloth bag was placed outside a film, the resulting product has a sufficient effectiveness as a warmer and also, temperature and duration time could be optionally selected by varying the amount of air permeation.

Table 3

| Experiment No. | 1 | 2 | 3 | 4 | 5 |
|---|---|---|---|---|---|
| Hole diameter (mmφ) | 3 | 3 | 3 | 3 | 3 |
| Number of hole | 2 | 25 | 50 | 100 | 150 |
| Effective amount of air permeation (cc/cm². min.) | 0.3 | 4.6 | 9.2 | 18.4 | 27.6 |

Table 4

| Experiment No. | 1 | 2 | 3 | 4 | 5 |
|---|---|---|---|---|---|
| Temperature (°C) | 29–32 | 51–55 | 53–57 | 67–70 | 80–85 |

Table 4-continued

| Experiment No. | 1 | 2 | 3 | 4 | 5 |
|---|---|---|---|---|---|
| Duration time (Hr.) | 37 | 22 | 21 | 10 | 6 |

Note: The duration time shows those lasted at temperatures of 37°C or higher, but in case of temperatures lower than 37°C, it is a time lasted at indicated temperature.

EXAMPLE 4

A heat-generating warmer bag having a construction shown in FIG. 4 was prepared using the following materials:

As a heat-generating composition, 25 g of iron powder (44μ), 1.5 g of NaCl (44μ), 10 g of active carbon (44μ) and 10 g of water were used. Water was used in the state absorbed in the active carbon.

Figure 6:
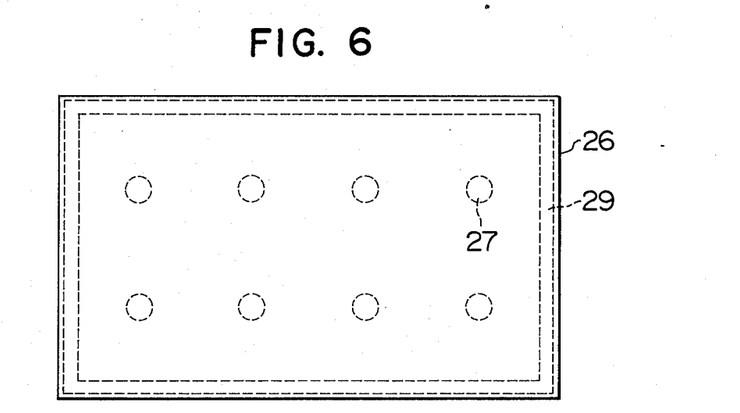
FIG. 6 is a plan view of the warmers of the present invention according to the embodiments of FIGS. 4 and 5.

A polyethylene film having a dimension of 150 mm × 100 mm and a thickness of 100μ was used as an air-impermeable film. On a polyethylene film having similarly a dimension of 150 mm × 100 mm and a thickness of 100μ, but provided with 6 holes of 6 mmφ (the total area of the holes: 1.7 cm$^2$) as shown in FIG. 6, was laid a nylon non-woven cloth (dimension, 150 mm × 100 mm; weight, 40 g/m$^2$) manufactured by Asahi Kasei Kogyo Kabushiki Kaisha. The thickness of this cloth was 0.1 mm and its amount of air permeation was 5,880 cc/cm$^2$. min.

For sealing said heat-generating composition, the four corners of the non-woven cloth laid film were heat-sealed by means of an impulse sealer of FI-200-10 type (trade mark of a sealer manufactured by Fuji Seisakusho Co., Japan). The polyethylene film provided with the aeration holes and the non-woven cloth were, in advance, heat-sealed by means of said impulse sealer, and thereafter used. The resulting warmer bag had a weight of about 5 g and a thickness of 0.5 mm. Peeling test of adhered part was carried out, and the non-woven cloth was broken at the part not adhered. As for this warmer bag, a heat-generating average temperature of 45°–50°C lasted for 22 hours, and neither leakage nor scattering of powder out of the bag was observed.

This bag showed no change such as discoloration, peeling, etc. when allowed to stand for 6 months.

EXAMPLE 5

An experiment was carried out using a structure shown in FIG. 7.

As for the contained materials, 25.0 g of iron powder (reagent-grade; average size, 80μ; manufactured by Wako Junyaku Co., Japan) 4.0 g of ferric sulfate (reagent-grade, first grade; the average size and manufacturer are same as the above-mentioned), 30.0 g of active carbon (Yashicoal powder (trade mark) manufactured by Taihei Sangyo Co., Japan; 44μ), and 20.0 g of water (but water was used in the state impregnated on active carbon) were used after uniformly mixed.

As a bag, the one having a size of 80 mm × 130 mm in area for filling heat-generating composition was used. As for an air-permeable layer, a material obtained by adhering a polyethylene film (40μ thick; amount of air permeation, 2 × 10$^{-4}$ cc/cm$^2$. min.) onto both the surfaces of a flannel (0.9 mm thick; amount of air permeation, 540 cc/cm$^2$. min.), with Semedain 201 (trade mark of an adhesive agent manufactured by Semedainsha Co., Japan) was used. In a film, 25 holes of 0.071 cm$^2$ in area were bored as aeration holes. The effective amount of air permeation was 4.6 cc/cm$^2$. min. As a stupe layer, the one obtained by placing a flannel having a size of 80 mm × 130 mm (0.9 mm thick; amount of air permeation, 540 cc/cm$^2$. min.) inside and overlaying a double layer of gauze outside the flannel, was used. This layer was adhered onto the polyethylene film which forms the lower surface of the bag, with Semedain 201, and the resulting material was coated with Zenolplaster (trade mark, manufactured by Mikasa Seiyaku Co., Japan). The resulting material was put in a polyethylene bag (100 × 140 mm; 40μ thick; amount of air permeation, 2 × 10$^{-4}$ cc/cm$^2$. min.) as an outer bag, and after the air inside the outer bag was squeezed out, the outer bag was sealed. Even after the lapse of one week after the sealing, no heat-generation occurred.

The contents were taken out of the outer bag, and placed on a polyethylene sheet so as to make the stupe layer occupy the underside. A CA thermocouple was fixed thereon with an adhesive tape and temperature change was recorded by Multipen Recorder WA621-1 type. The room temperature at this time was 13–17°C. According to this measurement, temperatures of 49–56°C lasted for 15 hours.

A stupe having been heat-generated under the same conditions as those of the above-mentioned, and a usual non-heat-generating stupe were applied on both the shoulders of patients suffering stiff shoulders, the former being applied on one of shoulders and the latter on the other. As the result of application thereof to a number of patients, it was observed that in the case of the shoulder on which the heat-generating stupe was applied, the time to complete cure was shortened to about one-half to one-fourth.

EXAMPLE 6

Each of heat-generating compositions having blending ratios shown in Table 5 was put in a bag having a width of 170 mm and a length of 240 mm (material: laminate of nylon-polyethylene) and well mixed into a uniform mixture. A thermometer was inserted in the heat-generating composition from the opening, and further a glass tube having an inner cross-sectional area of 1 cm$^2$ and a length of 10 cm was attached. Thereafter other parts were closed by a cellotape (a cellophane adhesive tape), and then temperature of generated heat, its lasting time and others were measured.

Table 5

| | Heat-generating composition | | | | | |
|---|---|---|---|---|---|---|
| Experiment Material No. | 1 | 2 | 3 | 4 | 5 | 6 |
| Iron powder (g) | 25 | 25 | 25 | 25 | 25 | 25 |
| Ferric | | | | | | |

Table 5-continued

Heat-generating composition

| Experiment<br>Material No. | 1 | 2 | 3 | 4 | 5 | 6 |
|---|---|---|---|---|---|---|
| sulfate (g) | 1.3 | 1.3 | 1.3 | 1.3 | 1.3 | — |
| NaCl (g) | — | — | — | — | — | 1.3 |
| Active carbon (g) | — | 25<br>(295–104μ) | 0.6<br>(104μ or smaller) | 25<br>(104μ or smaller) | 105<br>(104μ or smaller) | 25<br>(104μ or smaller) |
| Water (g) | 2.5 | 25 | 0.6 | 25 | 105 | 25 |

Notes:
1. Active carbon and water were mixed together in advance in a glass vessel provided with a tight plug, and after tightly plugged, they were allowed to stand for 24 hours.
2. Iron powder: made by Wako Junyaku Co., 98% or more of 200 mesh
Ferric sulfate: made by Wako Junyaku Co., reagent grade, first grade
Active carbon: coconut shell charcoal made by Taihei Kagaku Co., Japan As a result, as seen in Table 6, it was found that by making the particle size of active carbon smaller, extension of the heat-generation time became possible and also the initial heat-generation became faster; and when the content of active carbon was less than 2.5 parts by weight per 100 parts by weight of iron powder, there was no smell-adsorbing effect, and when the content was more than 400 parts by weight, the temperature of heat-generation was lower and the heat-generating effect was smaller.

Table 6

Results of experiments

| Experiment No. | | 1 | 2 | 3 | 4 | 5 | 6 |
|---|---|---|---|---|---|---|---|
| Initial heat-generation speed (min.) | | 14 | 7 | 12 | 4 | 5 | 3 |
| Highest temperature of heat-generation (°C) | | 96 | 63 | 88 | 62 | 34 | 57 |
| Average temperature (°C) | | 89 | 60 | 85 | 58 | 31 | 45 |
| Duration time (min.) | 50°C or higher | 45 | 103 | 55 | 121 | — | — |
| | 30°C or higher | — | — | — | — | 108 | 120 |
| Smell | | Strong smell of iron rust | No | Yes | No | No | No |

Note: Initial heat-generation speed shows a time which elapsed from the contact with air after completion of mixing, to the rise of the temperature up to 30°C.

EXAMPLE 7

Each of the heat-generating compositions shown in Table 7 was put in 200 cc messcylinder up to its 200 cc mark line and the weight of the contents was measured. Just thereafter the contents were put in a polyethylene bag of 20 cm long, 10 cm wide and 500 cc capacity. Then, thermometers were set to the upper part (No.1), the middle part (No.2) and the lower part (No.3) of the heat-generating composition, through an opening, and further a glass tube having an inner cross-sectional area of 1 cm² and a length of 10 cm was attached to the opening. Thereafter, other parts were closed by a cellotape, and the outer periphery of the polyethylene bag was insulated with a polyurethane foam (2 mm thick). Thus, the temperature distribution, handle, deviation and separation state were observed. The results are shown in Table 8. As seen from this Table it was found that the material in which active carbon was smaller in particle size than 104μ and contained impregnated water, generated heat uniformly, and had a good handle, light weight, and showed neither deviation nor separation, and warmth-keeping time was remarkably prolonged.

Table 7

Heat-generating composition

| Experiment No.<br>Material | 7 | 8 | 9 | 10 |
|---|---|---|---|---|
| Iron powder (98% or more of 200 mesh pass) (part by weight) | 100 | 100 | 100 | 100 |
| Ferric sulfate (part by weight) | 5 | 5 | 5 | 5 |
| Active carbon (part by weight) | — | 50<br>(295–147μ) | 50<br>(104μ pass) | 50<br>(104μ pass) |
| Water (part by weight) | 10 | 50 | 50 | 125 |

Table 8

Result of measurement

| Experiment No.<br>Kind of measurement | | 7 | 8 | 9 | 10 |
|---|---|---|---|---|---|
| Heat generating composition | Apparent s.g. (g/cc) | 2.00 | 1.54 | 0.47 | 0.50 |
| | Weight (g) | 400 | 308 | 94 | 100 |
| Average temperature (°C) | | 86 | 60 | 58 | 58 |
| Temperature distribution (°C) | No. 1 | 88 | 62 | 59 | 58 |
| | No. 2 | 86 | 60 | 58 | 58 |
| | No. 3 | 83 | 57 | 58 | 57 |
| Duration time of 50°C or higher (hr.) | | 4 | 1 | 18 | 22 |

Table 8-continued

Result of measurement

| Kind of measurement | Experiment No. | 7 | 8 | 9 | 10 |
|---|---|---|---|---|---|
| Handle | | Stiff and Weight feeling | Weight feeling | Soft and good handle | Soft and good handle |
| Deviation and separation | | Yes | Yes | No | No |

Notes:
1. For "deviation" and "separation", a heat-generating composition contained in a bag was dropped three times from a height of 10 cm and the movement of the heat-generating composition was determined. If the movement becomes half the initial height, the resulting case was regarded as "Deviation: Yes", and thereafter separation state was observed by naked eyes.
2. "Handle" was judged by finger-touch and skin-touch from the outside of the bag.

EXAMPLE 8

Figure 10:
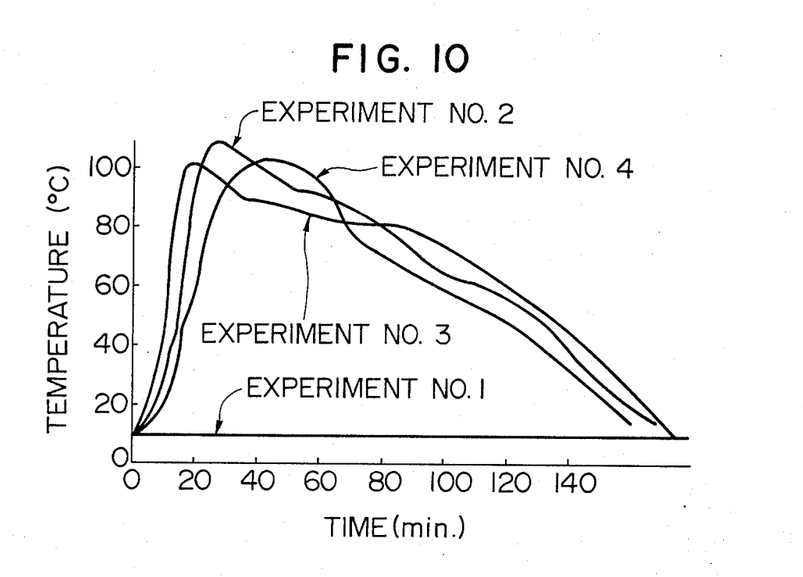
FIG. 10 is a graph showing the heat-generating status in case of example 8.
Figure 11:
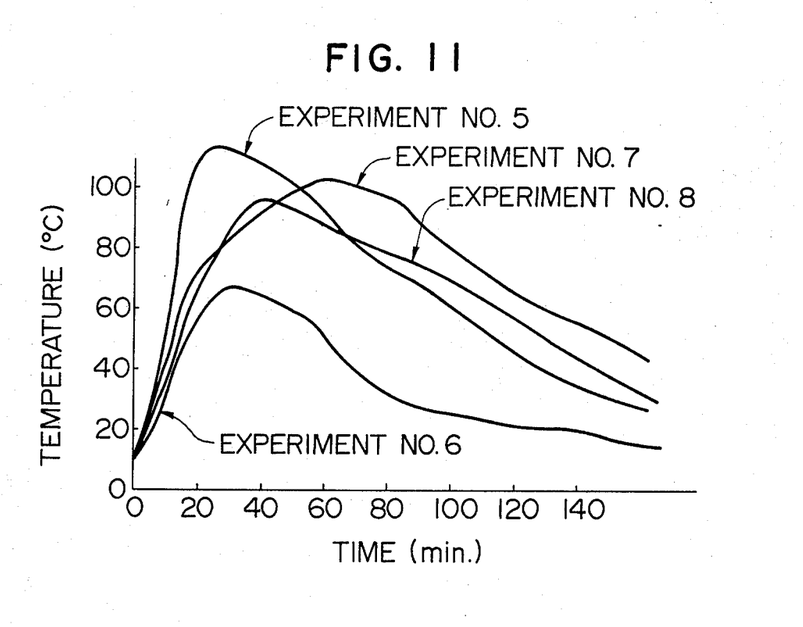
FIG. 11 is a cross-sectional view of one embodiment of the warmers of the present invention as mentioned above.

Each of the heat-generating compositions shown in Table 9 was put in a heat-resistant, hard polyethylene bag of 20 cm long, 10 cm wide and 500 cc capacity, from the opening at one end of the bag in the direction of length. Then, water was added. After the content was uniformly mixed, a chromel-alumel thermocouple was inserted from the opening of the bag, and further a glass tube for introducing air, having an inner cross-sectional area of 1 cm² and 2 cm length, was attached to the opening. Thereafter the opening was closed and the heat-generating state of the heat-generating composition was recorded by Multipen Recorder WA621-1 type. The results are shown in FIG. 10 and FIG. 11.

Table 9

Heat-generating composition

| Experiment No. | Raw material Iron powder (g) | Reaction auxiliary agent (g) | Heat-generating catalyst | |
|---|---|---|---|---|
| 1 | 100 | 5 | No addition | |
| 2 | 100 | 5 | Cu | 80 ppm |
| 3 | 100 | 5 | Cr | 100 ppm |
| 4 | 100 | 5 | Mn | 500 ppm |
| 5 | 100 | 5 | CuCl₂ | 100 mg |
| 6 | 100 | 5 | K₂CrO₄ | 100 mg |
| 7 | 100 | 5 | CuCrO₄ | 100 mg |
| 8 | 100 | 5 | MnSO₄ | 100 mg |

Notes:
1. Iron powders having a composition of Fe content 99.3%, Si content 0.65%, C content 24 ppm, Cr content 50 ppm and Mn content 71 ppm, and particle sizes of 124–147μ 11.5%, 104–124μ 17.5%, 74–104μ 40.5% and 61–74μ 30.5%, respectively were used.
2. As the reaction auxiliary agent, potassium chloride of 103μ in particle size and reagent grade, first grade, was used throughout these Experiments.
3. As the heat-generating catalyst, metal powder of 124–147μ in particle size and anhydrous salt of 103μ in particle size were used.

What is claimed is:

1. A unified structure of a warmer and an air-tight envelope which is used to encapsulate sealingly said warmer at non-service time, said warmer comprising means for enclosing an exothermic composition in contact with water, said means comprising a two layered bag composed of at least one air-permeable cloth layer and at least one impermeable film layer having aeration holes with a predetermined total area and arranged one within the other; said enclosing means being disposed within said air-tight envelope; and said exothermic composition which is activated on contact with air being selected from the group consisting of iron powder, a chloride and a sulfate of a metal having an ionization tendency greater than iron and active carbon filled in said bag, whereby upon opening of said airtight envelope, air contacts said exothermic composition and water to produce heat.

2. A unified structure of claim 1 wherein said film having aeration holes provides the amount of air permeation as measured by the air permeation test according to Frazier type method is in the range of 0.5–400 cc/cm². min.

3. A unified structure of claim 1 wherein said cloth is a non-woven fabric.

4. A unified structure of claim 1 wherein said chloride of a metal having an ionization tendency greater than iron is one member selected from the group consisting of KCl, NaCl, CaCl₂ and MgCl₂ in an amount of 0.5–30 parts by weight per 100 parts by weight of iron powder.

5. A unified structure of claim 1 wherein said sulfate of a metal having an ionization tendency greater than iron is one member selected from the group consisting of K₂SO₄, Na₂SO₄, MgSO₄ and Fe₂(SO₄)₃ in an amount of 2.5–400 parts by weight per 100 parts by weight of iron powder.

6. A unified structure of claim 1 wherein said active carbon has a particle size of 104μ or smaller and is used in an amount of 2.5–400 parts by weight per 100 parts by weight of iron powder.

7. A unified structure of claim 1 wherein water is used in an amount of 30–1,000 parts by weight per 100 parts by weight of iron powder.

8. A unified structure of claim 1 wherein iron powder has a particle size of 200μ or smaller.

9. A unified structure of claim 1 wherein said air-tight envelope is a laminate of synthetic resin films.

10. A unified structure of claim 1 wherein said air-tight envelope is a laminate of a synthetic resin film and an aluminum foil.

11. The structure of Claim 1 wherein said cloth layer is disposed within said film layer.

12. The structure of Claim 1 wherein said film layer is disposed within said cloth layer.

13. A unified structure of a warmer and an air-tight envelope, said warmer comprising means for enclosing an exothermic composition in contact with water, said means comprising a three layered bag composed of at least one air permeable cloth layer, a stupe layer provided on one side of said bag, and at least one impermeable film layer having aeration holes with a predetermined total area and arranged one within the other; said enclosing means being disposed within said air-tight envelope; and said exothermic composition which is activated in contact with air being selected from the group consisting of iron powder, a chloride and a sulfate of a metal having an ionization tendency greater than iron, and active carbon, filled in said bag, whereby upon opening of said airtight envelope air contacts said exothermic composition and water to produce heat.

14. A unified structure of claim 13 wherein said airtight envelope is a laminate of synthetic resin films.

15. A unified structure of claim 13 wherein said airtight envelope is a laminate of a synthetic resin film and an aluminum foil.

* * * * *